United States Patent
Wu et al.

(10) Patent No.: US 11,198,683 B2
(45) Date of Patent: Dec. 14, 2021

(54) METHOD FOR PREPARING TYROSINE KINASE INHIBITOR AND DERIVATIVE THEREOF

(71) Applicant: Jiangsu Hengrui Medicine Co., Ltd., Jiangsu (CN)

(72) Inventors: Guaili Wu, Jiangsu (CN); Quanliang Zhang, Jiangsu (CN); Yongxing Cao, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 0 days.

(21) Appl. No.: 17/005,489

(22) Filed: Aug. 28, 2020

(65) Prior Publication Data

US 2020/0392111 A1    Dec. 17, 2020

Related U.S. Application Data

(62) Division of application No. 16/094,278, filed as application No. PCT/CN2017/082164 on Apr. 27, 2017, now Pat. No. 10,793,548.

(30) Foreign Application Priority Data

Apr. 28, 2016  (CN) .......................... 201610274566.2

(51) Int. Cl.
| | | |
|---|---|---|
| *C07D 207/08* | (2006.01) | |
| *C07D 401/14* | (2006.01) | |
| *C07D 207/16* | (2006.01) | |
| *C07D 401/12* | (2006.01) | |

(52) U.S. Cl.
CPC ......... *C07D 401/14* (2013.01); *C07D 207/08* (2013.01); *C07D 207/16* (2013.01); *C07D 401/12* (2013.01); *Y02P 20/55* (2015.11)

(58) Field of Classification Search
CPC .................................................. C07D 207/08
See application file for complete search history.

(56) References Cited

U.S. PATENT DOCUMENTS

| | | |
|---|---|---|
| 7,126,025 B2 | 10/2006 | Considine |
| 7,399,865 B2 | 7/2008 | Wissner |
| 9,353,062 B2 | 5/2016 | Zhang |

FOREIGN PATENT DOCUMENTS

| | | |
|---|---|---|
| CN | 1082543 A | 2/1994 |
| CN | 102933574 A | 2/2013 |
| CN | 104203242 A | 12/2014 |
| CN | 105330646 A | 2/2016 |
| WO | 2006113837 A2 | 10/2006 |
| WO | 2010048477 A2 | 4/2010 |
| WO | 2011029265 A1 | 3/2011 |
| WO | 2015028409 A1 | 3/2015 |

OTHER PUBLICATIONS

Diederich et al. I, "Diasteroselective Zwitterionic, etc.," Chem.—Eur. J. 2(7), 894-900. (Year: 1996).*
Diederich et al. II, "Synthesis of optically, etc.," Angewandte Chemie, Int. Ed. Engl., 34(9), 1026-1028. (Year: 1995).*
Mali et al., "HBTU mediated, etc.," Org. Biomol. chem., 12, 8462-8472. (Year: 2014).*
Bohland et al., "Flexible Synthesis, etc.," Eur. J. Org. Chem., 6272-6284. (Year: 2014).*
Lundgren et al., "Catalytic Asymmetric, etc.," Angew. Chem. Int, Ed. 2525-2528 and Supporting InformationS-1 to S-34. (Year: 2013).*
Davies et al., "Asymmetric synthesis, etc.," Tetrahedron 69 1369-1377. (Year: 2013).*
Xiang et al., "One-pot, etc.," Chem. Commun., 7045-7047 and Supporting Information S-1 to S-25.. (Year: 2009).*
Clark et al., "Rearrangement of, etc.," J of the Chemical Society, Perkin Transactions 1, 3325-3337. (Year: 2001).*
List et al., "Efficient Proline, etc.," Organic Letters, 3(16), 2423-2425. (Year: 2001).*
Noguchi et al., "Chirality transfer, etc.," Tet. Letts., 41, 8489-8493. (Year: 2000).*
Int'l Search Report dated Jul. 11, 2017 in Int'l Application No. PCT/CN2017/082164.
Lundgren et al., "Catalytic Asymmetric C—N Bond Formation: Phosphine-Catalyzed Intra- and Intermolecular g-Addition of Nitrogen Nucleophiles to Allenoates an Alkynoates Angew," Angewandte Chemie International Edition in English, vol. 52, No. 9, pp. 2526-2635 (Dec. 2013).
Mishra et al., "Expeditious Synthesis of Imidazole- and Pyrrole-Fused Benzodiazocines," European Journal of Organic Chemistry, vol. 25, pp. 4832-4840 (Dec. 2010).
Chen, et al., "Synthesis of , etc.," CA 167:19662. (Year: 2014).
Zhou et al., "Process for the, etc.," CA 164:314869. (Year: 2016).
Dorwald, Side Reactions in Organic Synthesis, Wiley: VHC Weinheim Preface, pp. 1-15 & Chapter 8, pp. 279-308. (Year: 2005).

* cited by examiner

*Primary Examiner* — Patricia L Morris
(74) *Attorney, Agent, or Firm* — Ice Miller LLP

(57) ABSTRACT

A method for preparing a tyrosine kinase inhibitor and a derivative thereof are described. In particular, the present method has a short synthesis route, low costs, easy operation, and is suitable for large-scale production.

5 Claims, No Drawings

METHOD FOR PREPARING TYROSINE KINASE INHIBITOR AND DERIVATIVE THEREOF

CROSS-REFERENCE TO RELATED APPLICATIONS

This application is a divisional of U.S. application Ser. No. 16/094,278, filed Oct. 17, 2018, which is a Section 371 of International Application No. PCT/CN2017/082164, filed Apr. 27, 2017, which was published in the Chinese language on Nov. 2, 2017, under International Publication No. WO 2017/186140 A1, which claims priority under 35 U.S.C. § 119(b) to Chinese Application No. 201610274566.2, filed Apr. 28, 2016, the disclosures of which are incorporated herein by reference in their entirety.

FIELD OF THE INVENTION

The present invention relates to a method for preparing a tyrosine kinase inhibitor and a derivative thereof, and also relates to a new intermediate and a method for preparing the same.

BACKGROUND OF THE INVENTION

In recent years, cancer mortality in our country has increased obviously. The mortality of malignant tumors in urban residents is about 100-200/100,000. People's lives and quality of life are seriously threatened by cancer. With regard to malignant tumor proliferation, the chemotherapy with conventional chemotherapy drugs or the radiotherapy is highly toxic and has poor specificity. Therefore, it is a challenging and significant subject nowadays in the life sciences to search for anti-tumor drugs with high efficacy and low toxicity. Receptor tyrosine kinase is a class of transmembrane proteins involved in signal transduction. It is expressed in a variety of cells, for regulating cell growth, differentiation and neovascularization. Studies have shown that more than 50% of the proto-oncogene and oncogene products have tyrosine kinase activity, the abnormal expression of which causes tumorigenesis, and is also closely related to tumor invasion and metastasis, tumor neovascularization, and chemotherapy resistance of tumors. Tyrosine kinase inhibitors have been commercially available since 2001, and have become a new class of anticancer drugs that rise rapidly.

A number of tyrosine kinase inhibitors, such as Canertinib (CI-1033), BIBW-2992, Neratinib (HKI-272) and Pelitinib (EKB-569), have been disclosed in the prior art. Among them, Canertinib is the first to enter clinical trials, which was found to cause thrombocytopenia in phase II clinical trials. Therefore, research on Canertinib has been terminated. However, irreversible pan-ErbB inhibitors, such as PF-00299804 obtained by modification of Canertinib, have been developed continuously. Pre-clinical trials have demonstrated that PF-00299804 can inhibit the EGFR mutant T790M and the wild-type thereof, as well as HER-2 resistant to Gefitinib.

BIBW2992 is a novel drug developed by Pfizer as a first-line drug for the treatment of advanced non-small cell lung cancer (NSCLC).

Neratinib is a small molecule tyrosine kinase inhibitor developed by Puma Biotechnology under the license of Wyeth and Pfizer, and is used in patients with solid tumors, metastatic breast cancer, and non-small cell lung cancer who have been treated with Herceptin.

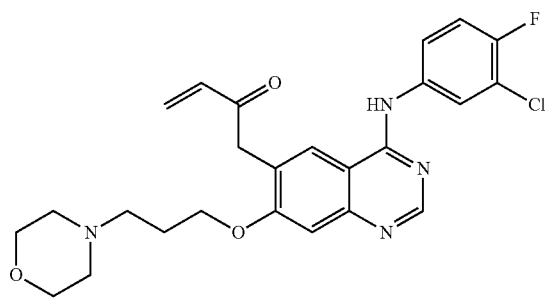
Canertinib

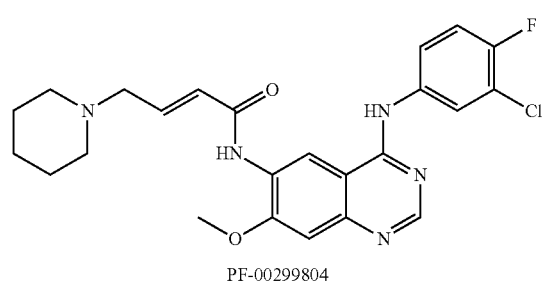
PF-00299804

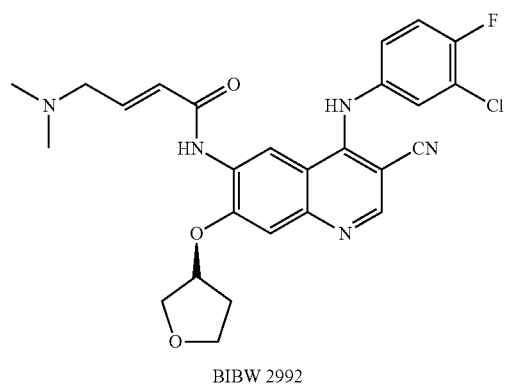
BIBW 2992

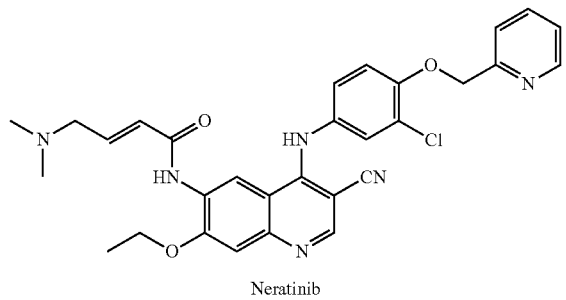
Neratinib

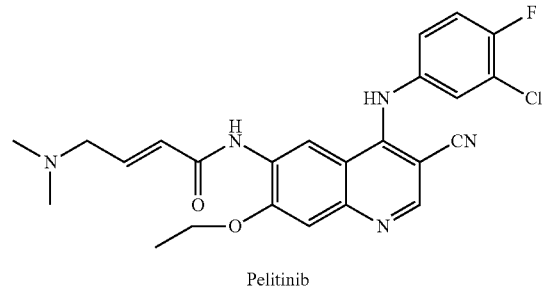
Pelitinib

WO2011029265 discloses an effective tyrosine kinase inhibitor and a preparation method thereof, its chemical name is (R,E)-N-(4-(3-chloro-4-(pyridin-2-ylmethoxy)phenylamino)-3-cyano-7-ethoxyquinoline-6-yl)-3-(1-methylpyrrolidin-2-yl)acrylamide, and its structure is as shown in formula I,

I

This compound has obvious pharmacodynamic advantages. CN102933574A discloses a dimaleate salt of the compound, which has improved physicochemical properties, pharmacokinetic properties, and bioavailability.

The method for preparing the compound of formula I disclosed in the prior art is as follows: 6-amino-4-[[3-chloro-4-(2-pyridylmethoxy)phenyl]amino]-7-ethoxy-quinoline-3-carbonitrile is reacted with diethyl phosphonoacetate, followed by reaction with 1-methylpyrrolidine-2-carbaldehyde to obtain the compound of formula I. The method has disadvantages such as complicated operation, high cost, low yield, low safety, and difficulty in scaling up the production.

SUMMARY OF THE INVENTION

In order to overcome the deficiencies of the prior art, the object of the present invention is to provide a method for synthesizing a tyrosine kinase inhibitor and a derivative thereof, which is more suitable for industrial production.

In one aspect, the present invention provides a compound of formula VI,

VI wherein $R_2$ is selected from the group consisting of hydrogen, an amino protecting group, cycloalkyl, cycloalkenyl, alkyl, alkenyl, alkynyl, aralkyl, and substituted or unsubstituted aryl or heteroaryl;

R is selected from the group consisting of hydroxy, —$OR_a$, and halogen; and $R_a$ is selected from the group consisting of alkyl, aryl, and alkylaryl, wherein the alkyl, aryl, and alkylaryl are each optionally substituted by a substituent.

In another aspect, the invention provides a method for preparing a compound of formula II or a pharmaceutically acceptable salt thereof,

II

III

IV wherein:

R is selected from the group consisting of hydroxy, —$OR_a$, and halogen;

$R_a$ is selected from the group consisting of alkyl, aryl, and alkylaryl, wherein the alkyl, aryl, and alkylaryl are each optionally substituted by a substituent;

$R_1$ is selected from the group consisting of hydrogen, cycloalkyl, cycloalkenyl, alkyl, alkenyl, alkynyl, aralkyl, and substituted or unsubstituted aryl or heteroaryl;

$R_2$ and $R_3$ are each independently hydrogen, an amino protecting group, cycloalkyl, cycloalkenyl, alkyl, alkenyl, alkynyl, aralkyl, or a substituted or unsubstituted aryl or heteroaryl group, or $R_1$ and $R_3$ together with the nitrogen to which $R_3$ is attached form a nitrogen-containing heteroaryl or heterocyclyl, or $R_2$ and $R_3$ together with the nitrogen to which $R_3$ is attached form a nitrogen-containing heteroaryl or heterocyclyl;

A is selected from the group consisting of a carbon atom and a nitrogen atom;

when A is a carbon atom, $R_5$ is selected from the group consisting of a hydrogen atom and alkyl, wherein the alkyl is optionally substituted by one or more substituents selected from the group consisting of halogen and alkoxy, and $R_6$ is cyano;

when A is a nitrogen atom, $R_5$ is selected from the group consisting of a hydrogen atom and alkyl, wherein the alkyl is optionally substituted by one or more substituents selected from the group consisting of halogen and alkoxy, and $R_6$ is unsubstituted;

$R_4$ has the following structure:

wherein:

D is selected from the group consisting of aryl and heteroaryl, wherein the aryl and heteroaryl are each independently and optionally substituted by one or more substituents selected from the group consisting of halogen, alkyl and trifluoromethyl;

T is selected from the group consisting of —(CH$_2$)r-, —O(CH$_2$)r-, —NH(CH$_2$)r-, and —S(CH$_2$)r;

L is selected from the group consisting of aryl and heteroaryl, wherein the aryl and heteroaryl are each independently and optionally substituted by one or more halogen or alkyl; and r is 0, 1 or 2, the method comprises a step of reacting a compound of formula IV with a compound of formula III.

The compound of formula IV can also be introduced into the reaction in the form of an acid addition salt thereof, for example, a hydrochloride salt and the like, to facilitate the feeding process.

In a preferred embodiment of the present invention, R is hydroxy, and the compound of formula IV can be reacted with the compound of formula III in the presence of a condensing agent, wherein the condensing agent can be a conventional condensing agent, for example, one or more of DCC, EDC, BOP, HBTU, and EEDQ, preferably EEDQ.

The solvent for the reaction can be one or more of pyridine, quinoline, acetonitrile, N-methylpyrrolidone, dichloromethane, ethyl acetate, tetrahydrofuran, N,N-dimethylformamide, and N,N-dimethylacetamide, preferably N-methylpyrrolidone. The reaction is preferably carried out at 20-30° C. In another preferred embodiment of the present invention, R is a halogen, preferably chlorine. The method also comprises a step of reacting a compound of formula V with an acyl halogenating reagent to obtain a compound of formula IV.

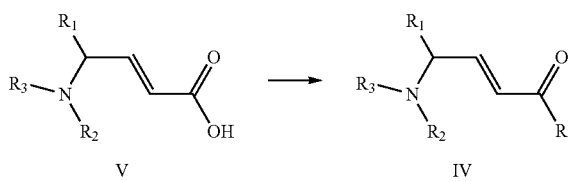

The acyl halogenating reagent can be one or more of oxalyl chloride, phosphorus halide, thionyl halide, and triphenylphosphine halide. The solvent for the two reactions can be one or more of pyridine, quinoline, acetonitrile, N-methylpyrrolidone, dichloromethane, ethyl acetate, tetrahydrofuran, N,N-dimethylformamide, and N,N-dimethylacetamide, preferably N-methylpyrrolidone.

Further, the compound of formula II can be a compound of formula I, the compound of formula III can be a compound of formula VII, and the compound of formula IV can be a compound of formula VI,

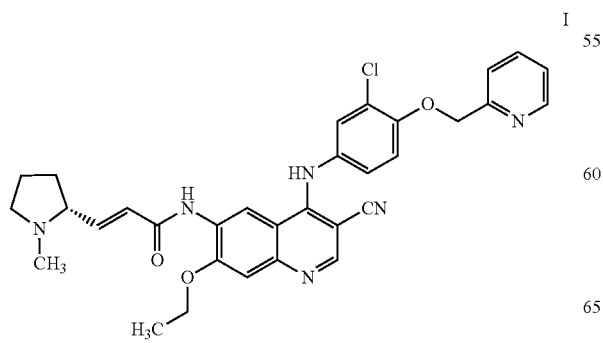

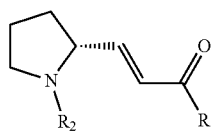

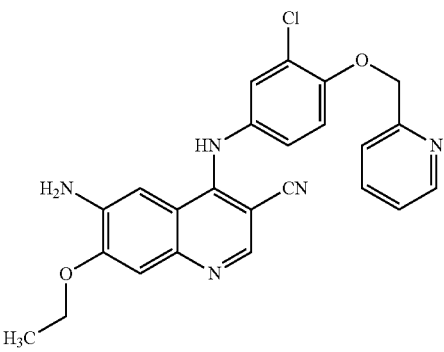

wherein R$_2$ is selected from the group consisting of hydrogen, an amino protecting group, cycloalkyl, cycloalkenyl, alkyl, alkenyl, alkynyl, aralkyl, and substituted or unsubstituted aryl or heteroaryl;

R is selected from the group consisting of hydroxy, —OR$_a$, and halogen; and

R$_a$ is selected from the group consisting of alkyl, aryl, and alkylaryl, wherein the alkyl, aryl, and alkylaryl are each optionally substituted by a substituent.

The pharmaceutically acceptable salt of the compound of formula I can be p-toluenesulfonate salt, methanesulfonate salt, maleate salt, succinate salt or malate salt, preferably maleate salt, and more preferably dimaleate salt. The above salts of the compound of formula I can be prepared by a method disclosed in the prior art (for example CN102933574A).

Further, the compound of formula II can be Neratinib, the compound of formula III can be a compound of formula VII, and the compound of formula IV can be a compound of formula IX,

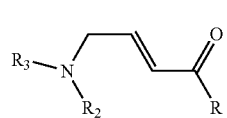

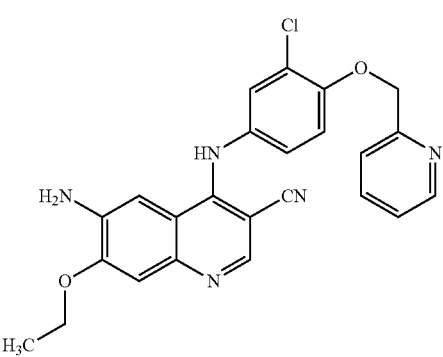

wherein R is selected from the group consisting of hydroxy, —OR$_a$, and halogen;

$R_a$ is selected from the group consisting of alkyl, aryl, and alkylaryl, wherein the alkyl, aryl, and alkylaryl are each optionally substituted by a substituent; and $R_2$ and $R_3$ are each independently hydrogen, an amino protecting group, cycloalkyl, cycloalkenyl, alkyl, alkenyl, alkynyl, aralkyl, and substituted or unsubstituted aryl or heteroaryl.

In another aspect, the present invention provides a method for preparing a compound of formula VI, comprising a Wittig-Horner reaction between a compound of formula VIII and phosphoryl carboxylate to obtain a compound of formula X,

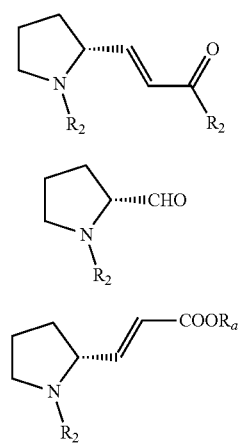

wherein $R_2$ is selected from the group consisting of hydrogen, an amino protecting group, cycloalkyl, cycloalkenyl, alkyl, alkenyl, alkynyl, aralkyl, and substituted or unsubstituted aryl or heteroaryl;

R is selected from the group consisting of hydroxy, —$OR_a$, and halogen; and $R_a$ is selected from the group consisting of alkyl, aryl, and alkylaryl, wherein the alkyl, aryl, and alkylaryl are each optionally substituted by a substituent, and the phosphoryl carboxylate is preferably triethyl phosphonoacetate.

In a preferred embodiment of the present invention, R is hydroxy or halogen, the method also comprises a step of hydrolyzing the compound of formula X in the presence of an alkaline medium, the alkaline medium is one or more selected from the group consisting of $Et_3N$, DBU, TMG, Py, DIPEA, $K_2CO_3$, $KHCO_3$, $Na_2CO_3$, $NaHCO_3$, KOH, NaOH, NaOMe, NaOEt, NaOtBu, and NaH, preferably KOH.

Further, when R is chlorine, the method also comprises a step of reacting the product obtained by hydrolysis in the previous step with an acyl halogenating reagent, the acyl halogenating reagent is one or more selected from the group consisting of oxalyl chloride and thionyl chloride.

The method for preparing a tyrosine kinase inhibitor and a derivative thereof according to the present invention has the advantages of safe and simple operation, high optical purity of the product, safe reaction reagent, milder reaction conditions, lower cost, and is suitable for industrial production. The reaction results are superior to the prior art, with significant social and economic benefits. The process of condensation reaction using a condensing agent can be carried out at room temperature, column chromatography is avoided which simplifies the post-treatment process, the reaction is easy to monitor, the feeding amount is optimized to reduce the cost, the reaction is stable and easy to reproduce, and the like, therefore, the method is more suitable for industrial scale production.

"Amino protecting group" refers to a suitable group known in the art for protecting an amino group, such as the amino protecting groups disclosed in the document ("Protective Groups in Organic Synthesis", $5^{Th}$. Ed. T. W. Greene & P. G. M. Wuts). Preferably, the amino protecting group can be ($C_{1-10}$ alkyl or aryl)acyl, for example, formyl, acetyl, benzoyl and the like; it can be ($C_{1-6}$ alkyl or $C_{6-10}$ aryl) sulfonyl; or it can also be ($C_{1-6}$ alkoxy or $C_{6-10}$ aryloxy) carbonyl, Boc or Cbz.

"Alkyl" refers to a linear or branched saturated aliphatic hydrocarbon group having 1 to 20 carbon atoms, preferably an alkyl group having 1 to 10 carbon atoms, for example, methyl, ethyl, propyl, 2-propyl, n-butyl, isobutyl, tert-butyl, pentyl and the like, and more preferably a lower alkyl group having 1 to 6 carbon atoms, for example methyl, ethyl, propyl, 2-propyl, n-butyl, isobutyl, tert-butyl, pentyl, heptyl and the like. The alkyl can be substituted or unsubstituted. When the alkyl is substituted, the substituent is preferably one or more groups independently selected from the group consisting of alkoxy, halogen, hydroxy, nitro, cyano, cycloalkyl, heterocyclyl, aryl, heteroaryl, and carbonyl.

"Aryl" refers to a 6 to 14-membered all-carbon monocyclic ring or polycyclic fused ring (i.e. each ring in the system shares an adjacent pair of carbon atoms with another ring in the system) having a conjugated π-electron system, preferably 6 to 10-membered aryl, more preferably phenyl and naphthyl, and most preferably phenyl. The aryl can be substituted or unsubstituted. When the aryl is substituted, the substituent is preferably one or more groups independently selected from the group consisting of alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio, and heterocycloalkylthio.

"Heteroaryl" refers to a heteroaromatic system comprising 1 to 4 heteroatoms and 5 to 14 ring atoms, wherein the heteroatom comprises O, S and N. The heteroaryl is preferably 6 to 10-membered. The heteroaryl is preferably 5 or 6-membered, for example, furanyl, thienyl, pyridyl, pyrrolyl, N-alkylpyrrolyl, pyrimidinyl, pyrazinyl, imidazolyl, tetrazolyl and the like. The heteroaryl ring can be fused to an aryl, heterocyclyl or cycloalkyl ring, wherein the ring bound to the parent structure is the heteroaryl ring. The heteroaryl can be optionally substituted or unsubstituted. When the heteroaryl is substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, heterocycloalkylthio, carbonyl, carboxy, and alkoxycarbonyl.

"Heterocyclyl" refers to a 3 to 20-membered saturated or partially unsaturated monocyclic or polycyclic hydrocarbon group having one or more heteroatoms selected from the group consisting of N, O, and $S(O)_n$ (wherein n is an integer of 0 to 2) as ring atoms, but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms, more preferably 3 to 10 ring atoms. Nonlimiting examples of monocyclic heterocyclyl include pyrrolidinyl, piperidyl, piperazinyl, morpholinyl, thiomorpholinyl, homopiperazinyl and the like. Polycyclic heterocyclyl includes a heterocyclyl having a spiro ring, fused ring or bridged ring.

"Alkoxy" refers to an —O-(alkyl) or an —O-(unsubstituted cycloalkyl) group, wherein the alkyl is as defined above. Nonlimiting examples include methoxy, ethoxy, propoxy, butoxy, cyclopropyloxy, cyclobutyloxy, cyclopentyloxy, cyclohexyloxy and the like. The alkoxy can be optionally substituted or unsubstituted. When the alkoxy is substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, heterocycloalkylthio, carbonyl, carboxy, and alkoxycarbonyl. "Hydroxy" refers to an —OH group.

"Optional" or "optionally" means that the event or circumstance described subsequently can, but need not, occur, and this description includes the situation in which the event or circumstance does or does not occur. For example, "a heterocyclic group optionally substituted by an alkyl" means that an alkyl group can be, but need not be, present, and this description includes the situation of the heterocyclic group being substituted by an alkyl and the situation of the heterocyclic group being not substituted by an alkyl.

Unless otherwise stated, the English abbreviations used in the specification and claims have the following meanings.

| Abbreviations | Full name |
| --- | --- |
| Et₃N | Triethylamine |
| DBU | 1,8-Diazabicyclo[5.4.0]undec-7-ene |
| TMG | N,N,N',N'-tetramethylguanidine |
| Py | Pyridine |
| DIPEA | Diisopropylethylamine |
| NaOMe | Sodium methoxide |
| NaOEt | Sodium ethoxide |
| NaOtBu | Sodium tert-butoxide |
| PCC | Pyridinium chlorochromate |
| EEDQ | 2-Ethoxy-1-ethoxycarbonyl-1,2-dihydroquinoline |
| DMAC | N,N-dimethylacetamide |

DETAILED DESCRIPTION OF THE INVENTION

The present invention is described in detail with reference to the following specific examples so that those skilled in the art will understand the present invention in a more comprehensive manner. The specific examples are used only to illustrate the technical solution of the present invention, but are not used to limit the scope of the present invention in any way.

EXAMPLE 1: PREPARATION OF COMPOUND 5

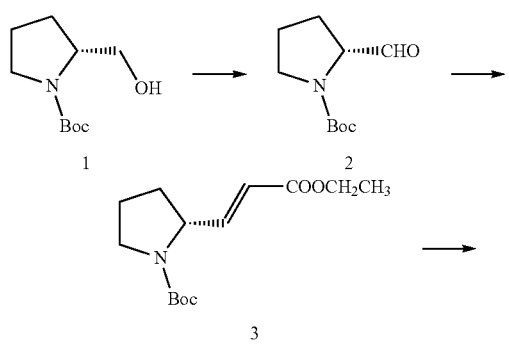

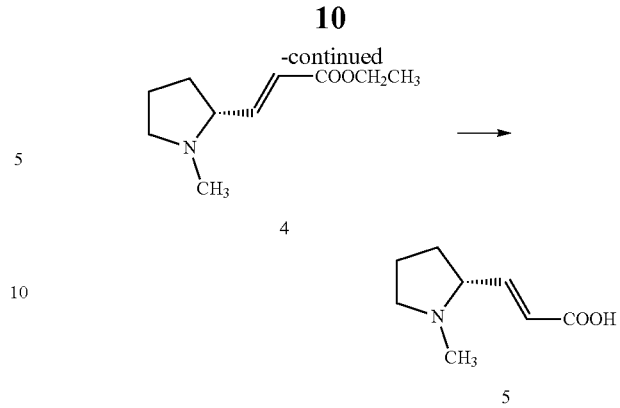

Step 1):

8.0 kg of compound 1, 264 kg of dichloromethane, and 13.0 kg of anhydrous sodium acetate were added to a 300 L reactor and stirred. The reaction system was cooled to 0° C. by freezing brine. 17.14 kg of PCC was then added in batches under nitrogen protection. After the completion of the addition, the freeze was stopped, and the reaction was carried out for 5 h with the temperature rising naturally. After the completion of the reaction was determined by TLC detection (ethyl acetate: petroleum ether=1:3), the mixture was filtered, and the filtrate was concentrated under reduced pressure to obtain a black oil. The product was eluted over column chromatography (the eluent was ethyl acetate: petroleum ether=1:3). The main fraction was collected, concentrated under reduced pressure, and dissolved by addition of 64 kg of ethyl acetate. The solution was washed with 0.5 N diluted hydrochloric acid solution, water and saturated brine successively, dried over anhydrous sodium sulfate, and concentrated to obtain 6.42 kg of pale yellow oil.

114 kg of dichloromethane and 3.05 kg of 60% sodium hydride were added to a 300 L reactor and stirred well, and the mixture was cooled by freezing brine. 7.66 kg of triethyl phosphonoacetate was slowly added dropwise, and the addition was completed within about 30 min. The mixture was stirred at room temperature until no bubbles were produced. A solution of 6.4 kg of compound 2 obtained in the previous step in dichloromethane (85 kg) was added slowly dropwise, and the addition was completed within about 1 h. Then the reaction was carried out at room temperature for 1.5-2 h. After the completion of the reaction was determined by TLC detection, the mixture was cooled by freezing brine. An aqueous solution of ammonium chloride (1.26 kg of ammonium chloride dissolved in 4.0 kg of water) was added slowly until no bubbles were produced. The mixture was stirred for about 0.5 h. Purified water was then slowly added dropwise until the mixture was clear. Two phases were separated, and the aqueous phase was extracted once with dichloromethane. The organic phases were combined, washed with a saturated aqueous solution of sodium bicarbonate and saturated brine, dried over anhydrous sodium sulfate, and concentrated to obtain a crude ester product. The crude ester product was subjected to column chromatography (the eluent was ethyl acetate: petroleum ether=1:8). The main fraction was collected and concentrated to obtain 4.82 kg of compound 3, yield: 45.0%. (The TLC condition was petroleum ether: ethyl acetate=3:1, the $R_f$ of the product=0.7, the $R_f$ of the starting material=0.6).

Compound 3: $^1$H NMR (400 MHz, CDCl$_3$) δ=6.85-6.80 (dd, 1H), 5.84-5.80 (d, 1H), 4.40 (br, 1H), 4.22-4.17 (q, 2H), 3.42 (s, 2H), 2.08-2.06 (m, 1H), 1.89-1.82 (m, 2H), 1.79-1.73 (m, 1H), 1.44 (s, 9H), 1.31-1.27 (t, 3H) ppm.

MS (M+Na): 292.1

Step 2):

4.8 kg of compound 3 and 58.6 kg of formic acid were added to a 100 L reactor and stirred at room temperature for 15 min. 2.63 kg of paraformaldehyde was then added, and the mixture was heated to slightly reflux at 90° C. for 3-4 h until the starting material point disappeared by TLC detection. Most of the formic acid in the reaction solution was concentrated (about ⅕ remained), and 1M hydrochloric acid was added to adjust the pH to 1.0. The mixture was washed with ethyl acetate. The aqueous phase was further added with a saturated aqueous solution of potassium carbonate to adjust the pH to 8.0, and extracted with ethyl acetate. The organic phases were combined, washed with a saturated aqueous solution of sodium chloride, dried over anhydrous sodium sulfate, and filtered. The filtrate was concentrated to obtain 2.42 kg of compound 4, yield: 73.5%.

Compound 4: $^1$H NMR (400 MHz, CDCl$_3$) δ=6.85-6.80 (dd, 1H), 5.96-5.92 (d, 1H), 4.22-4.17 (q, 2H), 3.15-3.10 (m, 1H), 2.76-2.70 (m, 1H), 2.28 (s, 3H), 2.28-2.21 (m, 1H), 2.04-1.98 (m, 1H), 1.91-1.84 (m, 1H), 1.82-1.74 (m, 1H), 1.72-1.65 (m, 1H) ppm.

MS (M+1): 184.2

Step 3):

2.4 kg of compound 4 and then 5.9 kg of methanol were added to a 20 L reaction flask. 1.49 kg of potassium hydroxide was added in batches at a controlled temperature no more than 30° C., the addition was completed within about 1.5 h, and then the reaction was carried out at 30° C. for 2 h. After the completion of the reaction was determined by TLC detection, the pH was adjusted to 4-5 with 4N hydrochloric acid in methanol in an ice bath. The mixture was filtered, the filtrate was concentrated to dryness, and 2.7 kg of acetonitrile was added under stirring to precipitate a crystal. The mixture was filtered and dried to obtain 1.06 kg of compound 5, yield: 52.1%.

Compound 5: $^1$H NMR (400 MHz, d$^6$ DMSO) δ=12.60 (s, 1H), 11.72 (s, 1H), 6.94-6.88 (dd, 1H), 6.21-6.17 (d, 1H), 4.00 (s, 1H), 3.57 (s, 1H), 3.07 (s, 1H), 2.67 (s, 3H), 2.28-2.20 (m, 1H), 2.02-1.99 (m, 2H), 1.92-1.82 (m, 1H) ppm.

MS (M+1): 156.1

EXAMPLE 2: PREPARATION OF THE COMPOUND OF FORMULA I 1.0 kg of compound 5 and 9.4 kg of acetonitrile were added to a 20 L reaction flask, and then 30 g of N,N-dimethylformamide was added dropwise. 630 g of oxalyl chloride was slowly added dropwise in an ice bath. After the completion of the addition, the mixture was stirred at 20° C. for 5 h. A small amount of solid remained at the bottom of the reaction solution, and the reaction solution was directly used in the following condensation reaction without treatment.

1.15 kg of compound VII was dissolved in 7.2 kg of N-methylpyrrolidone and stirred for 10 min. The previous reaction solution was added dropwise in an ice bath, and the reaction was stirred at room temperature overnight. After the completion of the reaction was determined by TLC detection, the reaction solution was poured into warm water (45.0 kg) at about 40° C., and 10% sodium hydroxide solution was slowly added under stirring to adjust the pH to 10. The mixture was filtered to obtain a yellow solid. The resulting filter cake was pulped with warm water (about 5.0 kg) at 40° C., and then filtered. The filter cake was dissolved in dichloromethane to remove water, dried, concentrated, and purified by column chromatography with gradient elution, the starting eluent was dichloromethane: methanol=25:1, and finally increased to 15:1. The main fraction was collected and concentrated to obtain 1.12 kg of the compound of formula I, yield: 74.5%, with the HPLC purity of 99.71%.

Compound of formula I: $^1$H NMR (400 MHz, CDCl$_3$) δ=9.20 (s, 1H), 8.59-8.58 (t, 1H), 8.40 (s, 1H), 8.07-8.03 (d, 2H), 7.77-7.32 (m, 1H), 7.63-7.62 (d, 1H), 7.25-7.23 (q, 1H), 7.14 (s, 1H), 7.111-7.106 (d, 1H), 6.97-6.92 (q, 1H), 6.86-6.83 (q, 1H), 6.79-6.76 (q, 1H), 6.17-6.14 (d, 1H), 5.21 (s, 2H), 4.23-4.18 (q, 2H), 3.16-3.12 (m, 1H), 2.84-2.82 (d, 1H), 2.30-2.27 (t, 4H), 2.06-1.99 (m, 1H), 1.90-1.85 (m, 1H), 1.83-1.72 (m, 1H), 1.68-1.60 (m, 1H), 1.54-1.52 (t, 3H) ppm.

MS (M+1): 583.2

EXAMPLE 3: PREPARATION OF THE COMPOUND OF FORMULA I 2.0 kg of the compound of formula VII was dissolved in 20 L of N-methylpyrrolidone in a 50 L reactor. 1.2 kg of compound 5 and then 1.7 kg of EEDQ were added, and the reaction was stirred for 14-17 h at a controlled temperature of 20-25° C. 2.5 kg of water was slowly added in an ice bath, and the pH was adjusted to 9-10 with 5% aqueous NaOH solution (about 25 L). The mixture was filtered to obtain a product with a wet weight of about 4.9 kg. The resulting yellow solid was added with 30 kg of water, and 1 M HCl solution was added dropwise under stirring to adjust the pH to 2-5. The mixture was stirred until it was clear. The mixture was extracted with dichloromethane, the pH of the aqueous phase was adjusted to 9-10 with 5% aqueous NaOH solution, and the resulting solid was filtered to obtain a product with a wet weight of about 5.2 kg. 88.4 kg of ethanol and 8.8 kg of acetone were added, and the mixture was heated to reflux until it was clear. The solution was cooled to room temperature under stirring to precipitate a crystal for 15 h. The mixture was filtered, and the filter cake was washed with ethanol to obtain 2.1 kg of the compound of formula I as a pale yellow solid, yield: 80.3%, with the HPLC purity of 99.68%.

Since the present invention has been described based on the specific embodiments thereof, some modifications and equivalent variations are apparent to those skilled in the art and are within the scope of the present invention.

What is claimed is:

1. A compound of formula VI,

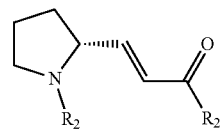

VI wherein R$_2$ is selected from the group consisting of an amino protecting group and alkyl; and R is hydroxy, wherein the amino protecting group is selected from the group consisting of (C$_{1-10}$ alkyl or aryl)-C(O)—, (C$_{1-6}$ alkyl or C$_{6-10}$ aryl) sulfonyl, (C$_{1-6}$ alkoxy or C$_{6-10}$ aryloxy) carbonyl and Cbz.

2. A method for preparing a compound of formula VI, comprising reacting a compound of formula VIII with a phosphoryl carboxylate in the presence of a base to obtain a compound of formula X,

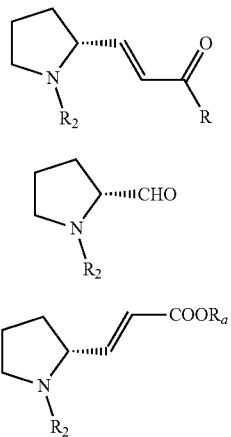

wherein $R_2$ is selected from the group consisting of an amino protecting group and alkyl;
R is hydroxy, and the phosphoryl carboxylate is triethyl phosphonoacetate; wherein the amino protecting group is selected from the group consisting of ($C_{1-10}$ alkyl or aryl)-C(O) ($C_{1-6}$ alkyl or $C_{6-10}$ aryl) sulfonyl, ($C_{1-6}$ alkoxy or $C_{6-10}$ aryloxy) carbonyl and Cbz.

3. The method for preparing the compound of formula VI according to claim 2, wherein R is hydroxy or halogen, and the method further comprises hydrolyzing the compound of formula X in the presence of an alkaline medium to obtain a hydrolysis product, wherein the alkaline medium is at least one selected from the group consisting of $Et_3N$, DBU, TMG, Py, DIPEA, $K_2CO_3$, $KHCO_3$, $Na_2CO_3$, $NaHCO_3$, KOH, NaOH, NaOMe, NaOEt, NaOtBu, and NaH.

4. The method for preparing the compound of formula VI according to claim 3, wherein R is chlorine, and the method further comprises reacting the hydrolysis product with an acyl halogenating reagent, wherein the acyl halogenating reagent is one or more selected from the group consisting of oxalyl chloride, phosphorus halide, thionyl halide, and triphenylphosphine halide.

5. The compound of formula VI according to claim 1, wherein the compound is

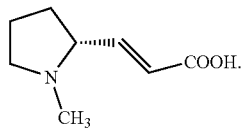

* * * * *